US007645069B1

(12) United States Patent
Fine et al.

(10) Patent No.: US 7,645,069 B1
(45) Date of Patent: Jan. 12, 2010

(54) ENERGETIC MATERIAL DETECTOR

(75) Inventors: David H. Fine, Cocoa Beach, FL (US); Herbert Duvoisin, III, Orlando, FL (US); Edward E. A. Bromberg, Orlando, FL (US); Steven Bullock, Orlando, FL (US); David P. Lieb, Lexington, MA (US); C. Andrew Helm, Oviedo, FL (US); Sean C. Christiansen, Orlando, FL (US); Eric Moy, Orlando, FL (US)

(73) Assignee: L-3 Communications Cyterra Corporation, Orlando, FL (US)

( * ) Notice: Subject to any disclaimer, the term of this patent is extended or adjusted under 35 U.S.C. 154(b) by 293 days.

(21) Appl. No.: 11/460,586

(22) Filed: Jul. 27, 2006

Related U.S. Application Data

(60) Provisional application No. 60/743,402, filed on Mar. 3, 2006, provisional application No. 60/743,083, filed on Dec. 29, 2005, provisional application No. 60/702,616, filed on Jul. 27, 2005.

(51) Int. Cl.
*G01N 25/50* (2006.01)
*G01N 25/54* (2006.01)
*G01N 33/22* (2006.01)
(52) U.S. Cl. .......................................... 374/8; 73/35.14
(58) Field of Classification Search ............. 374/10–12, 374/29–39, 14, 4–5, 43–45, 57, 141–144, 374/8, 120–121; 250/338.1; 73/35.14–35.17

See application file for complete search history.

(56) References Cited

U.S. PATENT DOCUMENTS

| 2,947,163 | A | * | 8/1960 | Stone | 374/10 |
| 3,593,563 | A | * | 7/1971 | Marmor et al. | 374/8 |
| 3,876,999 | A | * | 4/1975 | Lee | 340/521 |
| 4,023,201 | A | * | 5/1977 | Faulkner | 374/124 |
| 4,130,016 | A | * | 12/1978 | Walker | 374/34 |
| 4,166,385 | A | * | 9/1979 | Pate et al. | 374/31 |
| 4,266,219 | A | * | 5/1981 | Foster et al. | 340/630 |
| 4,533,258 | A | * | 8/1985 | Milovidov | 374/36 |
| 4,670,404 | A | * | 6/1987 | Swift et al. | 436/147 |
| 5,121,101 | A | * | 6/1992 | Jakubowski et al. | 340/515 |
| 5,163,753 | A | * | 11/1992 | Whiting et al. | 374/10 |
| 5,165,792 | A | * | 11/1992 | Crowe et al. | 374/10 |
| 5,346,306 | A | * | 9/1994 | Reading et al. | 374/10 |
| 5,552,257 | A | * | 9/1996 | Stewart et al. | 430/201 |
| 5,918,263 | A | * | 6/1999 | Thundat | 73/35.16 |
| 5,932,796 | A | * | 8/1999 | Arthaud et al. | 73/36 |
| 6,245,576 | B1 | | 6/2001 | Hiley | |

(Continued)

OTHER PUBLICATIONS

PCT International Preliminary Report on Patentability issued in International Application No. PCT/US2006/029301 mailed Sep. 4, 2008.

(Continued)

*Primary Examiner*—Gail Verbitsky
(74) *Attorney, Agent, or Firm*—Fish & Richardson P.C.

(57) ABSTRACT

A method of detecting energetic materials, such as explosives, includes energizing a sample area that contains particles of energetic materials. In the method, temperature characteristics from the sample area are monitored, and a temperature released from exothermic decomposition of the particles is detected. The method further includes analyzing the detected temperature to determine the presence of the exothermic compound which caused the decomposition.

41 Claims, 13 Drawing Sheets

U.S. PATENT DOCUMENTS

| | | | |
|---|---|---|---|
| 6,309,591 B1 * | 10/2001 | Yoo et al. | 266/249 |
| 6,406,918 B1 | 6/2002 | Bannister et al. | |
| 6,613,207 B1 | 9/2003 | De La Prieta | |
| 6,623,976 B1 * | 9/2003 | Hale et al. | 436/160 |
| 6,773,674 B2 | 8/2004 | Bannister et al. | |
| 6,803,577 B2 * | 10/2004 | Edner et al. | 250/339.09 |
| 2002/0008523 A1 | 1/2002 | Klang | |
| 2003/0031915 A1 * | 2/2003 | Diez et al. | 429/38 |
| 2004/0014233 A1 * | 1/2004 | Bannister et al. | 436/155 |
| 2004/0067302 A1 | 4/2004 | Burberry | |
| 2004/0185156 A1 | 9/2004 | Garwood | |
| 2004/0194548 A1 | 10/2004 | Dayagi | |
| 2005/0008063 A1 * | 1/2005 | Chippett | 374/34 |
| 2007/0086925 A1 * | 4/2007 | O'Donnell et al. | 422/100 |
| 2009/0044641 A1 * | 2/2009 | Konduri et al. | 73/863.11 |

OTHER PUBLICATIONS

International Search Report and the Written Opinion of the International Searching Authority issued in International Application No. PCT/US06/29301 on Jul. 18, 2008.

David H. Fine, "Spontaneous Ignition and Thermal Explosions", Sep. 1, 1967, Dissertation submitted in partial fulfillment of the requirement for the Degree of Doctor of Philosophy at the University of Leeds.

* cited by examiner

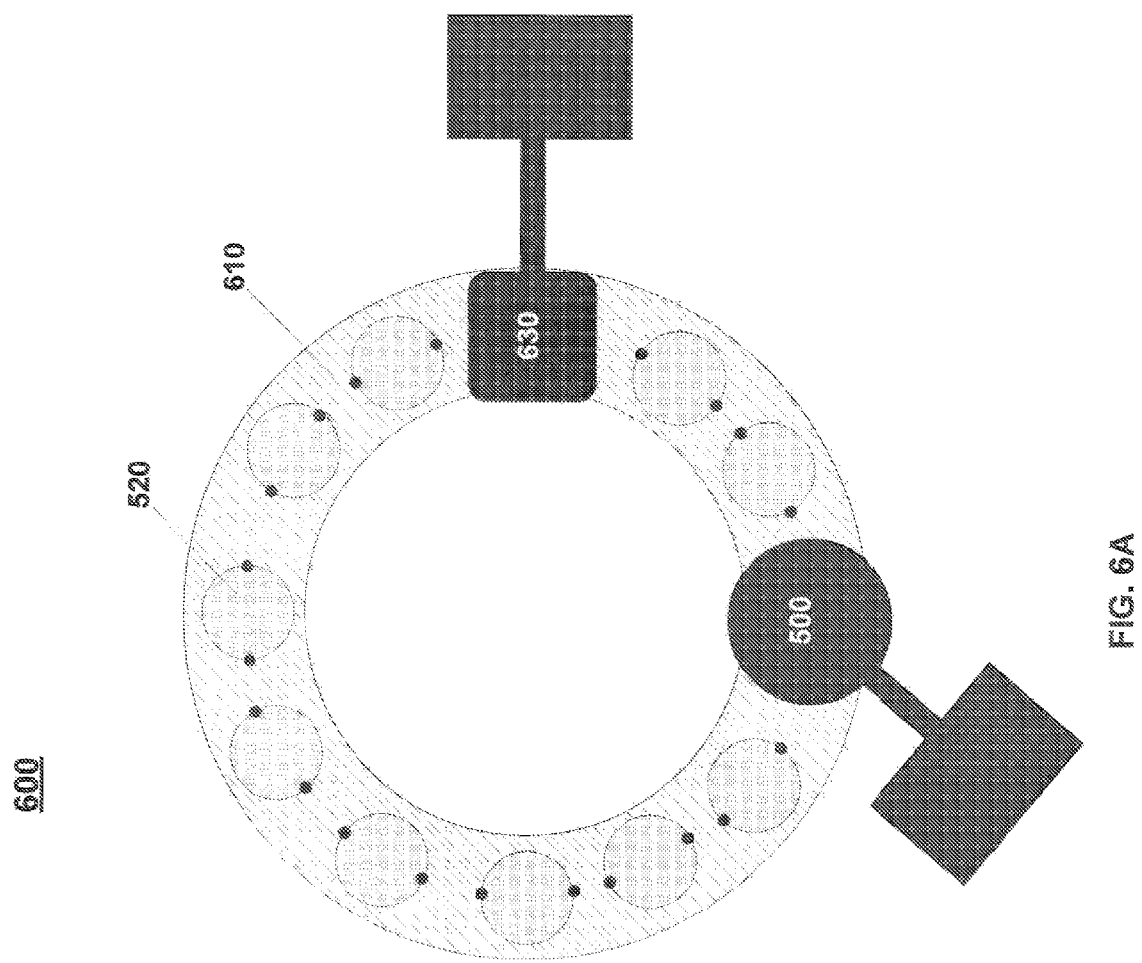

ENERGETIC MATERIAL DETECTOR

CROSS-REFERENCE

This application claims priority from U.S. Provisional Application Nos. 60/702,616, filed Jul. 27, 2005, and titled "Trace Explosives Detector Based Upon Detecting Exothermic Decomposition"; and 60/743,083, filed Dec. 29, 2005, and titled "Energetic Material Detector For Explosive Trace Detection"; and 60/743,402, filed Mar. 3, 2006, and titled "Energetic Material Detector For Explosive Trace Detection." Each of these applications is incorporated by reference.

TECHNICAL FIELD

This disclosure relates to detecting energetic materials, such as explosives.

BACKGROUND

In order to detect the presence of energetic materials, particles of the material may be analyzed.

SUMMARY

In one general aspect, detecting energetic materials, such as explosives, includes energizing a sample area that may contain particles of energetic materials. Temperature characteristics from the sample area are monitored, and a temperature released from exothermic decomposition of the particles is detected when particles of energetic materials are present. The monitored temperature characteristics are analyzed to determine whether the particles are present.

Implementations may include one or more of the following features. For instance, the sample area may be resistively heated. A current may be applied through a conductive collection material, such as a metal mesh. The applied current may be a step or ramp current.

The sample area also may be energized through radiative heating, such as with a flash-lamp or laser. The sample area may be radiatively heated from a distance beyond the adjacent vicinity of the device.

Infrared radiation may be monitored, and infrared radiation released from exothermic decomposition of materials may be detected. Temperature data may be analyzed for the difference between a pixel and a background temperature or the change with respect to time. The temperature data also may be analyzed to determine a heat of decomposition or an activation energy of the material that underwent exothermic decomposition. A determined heat of decomposition or activation energy may be used to determine a specific type or category of material, such as, triacetone triperoxide, that underwent exothermic decomposition.

Atmospheric oxygen available for combustion may be lowered. The air-pressure may be reduced and non-reactive gases may be introduced.

In another general aspect, a system for detecting energetic materials, such as explosives, includes a sample energizer configured to energize a sample that contains with particles of energetic materials. A sensor is configured to monitor temperature characteristics from the sample area and detect a temperature released from exothermic decomposition of the particles. An analyzing device is configured to analyze the detected temperature to determine the presence of an exothermic compound which caused the decomposition.

Implementations may include one or more of the features noted above.

The details of one or more implementations are set forth in the accompanying drawings and the description below. Other features and advantages will be apparent from the description and drawings, and from the claims.

DESCRIPTION OF DRAWINGS

FIGS. 6A and 6B illustrate a top and side view of a collection and detection system.

Like reference symbols in the various drawings indicate like elements.

DETAILED DESCRIPTION

Individuals have been able to conceal explosives by using unusual materials or precautionary methods to thwart detection. For example, while a traditional weapon, such as a grenade, may be detected on a person by means of a metal detector or in luggage by means of an x-ray scanner, explosives, such as, C-4 and TNT, may not be detected by such methods. Also, conventional explosive detection equipment may be designed detect certain known explosive material with specific chemical structures.

In order to screen a wider variety of potentially threatening material, trace sampling of particles may be used. Specifically, a sample of trace (e.g., microscopic) particles may be collected from an item or individual, and analyzed for properties indicative of explosives or threats. The analysis of particles may be conducted using a variety of mechanisms, such as an ion mobility detector (IMS), gas chromatography coupled with a chemiluminescence detector (GC-CL), or mass spectrometry. Many techniques are able to detect only specific chemicals, or chemicals with very specific types of chemical structures.

Whether a particle is an explosive may be determined by triggering a thermal decomposition (i.e., a thermal explosion) of the particle. In particular, explosive particles may be rapidly heated while monitoring for the presence of thermal decomposition. Various methods, such as resistive, conductive, radiative, or laser heating, may be used.

Resistive heating may be appropriate for systems where particles are collected and analyzed at close range. For example, a swipe or vacuum collection system may deposit particles on a steel mesh, which may be directly resistively heated. For long-range systems, radiative heating may be appropriate. For example, a radiative heater may be incorporated into a x-ray baggage scanner and may be used to detect explosive or other energetic particles from a range of less than a meter. Other systems may be radiatively heated and detected from much larger ranges, such as, for example, tens or hundreds of meters.

Figure 1:
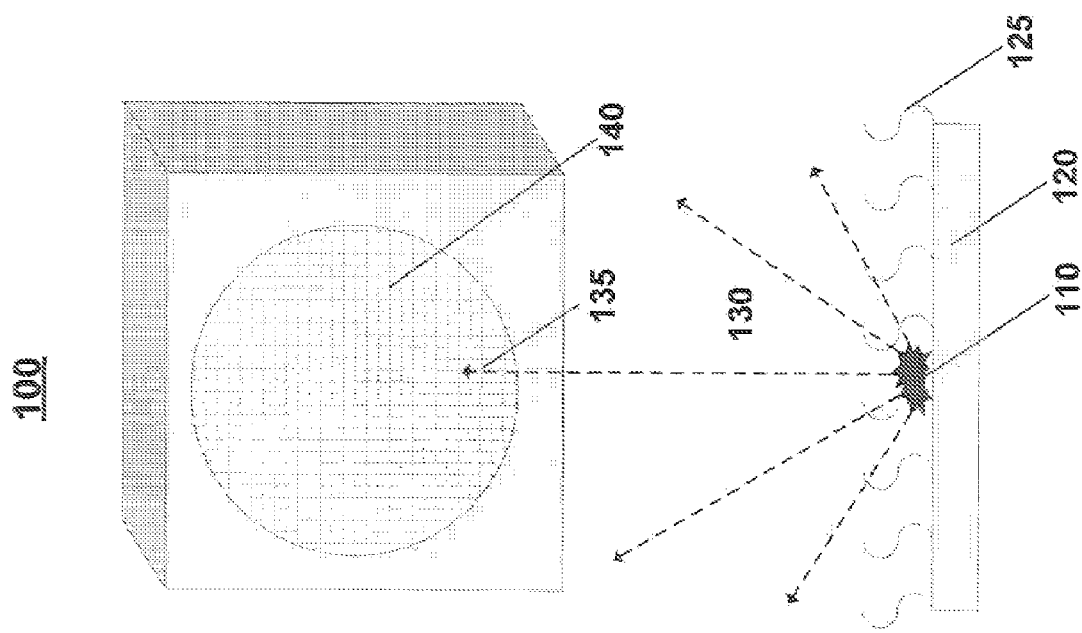
FIG. 1 illustrates a decomposition system.

Referring to FIG. 1, a detection system 100 analyzes a sample 110 using a collection material 120 and an infrared (IR) sensor 140. In the system 100, the sample 110 is placed on the collection material 120 and then heated 125 to trigger thermal decomposition. Energy 130 is released from the sample 110 during decomposition, and a portion 135 of that energy is detected by the IR sensor 140 to infer the presence of explosive particles.

The sample 110 may be collected from a variety of sources and by means of a variety of methods. In general, people who handle or work with explosives or other materials typically become contaminated with trace residues of the materials. For example, explosive particles may remain on the hands following manufacturing and/or handling of a bomb or explosive material, and some of these particles are may be transferred to the person's clothing. Such trace residue may also be transferred to items such as wallets, spectacles, keys, purses, and door handles, and these items may serve to re-contaminate the hands, even when they are washed and the individual changes clothing. The body, clothes, or articles may be swabbed by a collection device or vacuumed onto the collection material 120 to collect the trace residue as the sample 110 for analysis.

The collection material 120 may be constructed out of a variety of materials, such as, for example, Teflon, a stainless steel mesh, woven carbon fibers, a deactivated glass wool pad, a nichrome wire or ribbon, aluminum (and or stainless steel or nickel or other metals) coated polyimide, or carbon filled polyimide. If resistive heating is being employed, the collection material 120 may need to be conductive. If radiative heating is being employed, conductivity of the collection material 120 is not required.

Triggering thermal decomposition of the sample relies on the rapid kinetics and thermodynamics associated with the thermal decomposition of explosives. Although most molecules decompose endothermically when heated in an atmosphere deprived of oxygen, an explosive compound decomposes exothermically and releases heat to the environment. The released heat is immediately transferred to the molecules surrounding the decomposing explosives, which results in a localized increase in temperature that provides a measurable indicator of the presence and/or type of an explosive sample 110.

Specifically, explosive samples 110 decompose exothermically (they release heat to the surroundings) when heated anaerobically. If the mass of the explosives is large enough, the temperature rises, which accelerates the reaction rate even further, releasing additional heat, and culminating in a runaway thermal explosion. For sub-critical masses, the material is consumed before it explodes as heat is lost to the surroundings. Nevertheless, even for these sub-critical cases, the temperature rises above its surroundings before decaying back to the ambient.

The IR sensor 140 senses the portion 135 of the thermal energy 130 released during decomposition, which enables detection of explosives, including nitro-organics and nitro-salts, peroxides, perchlorates, and gun powder, as well as homemade explosives of as yet unknown composition. The IR sensor 140 employs an IR detection array to detect the thermal signature of the decomposition. In one implementation, the IR detection array is configured to detect heat in the mid-wave IR (MWIR), 3 to 5 micron wavelength, 5 to 8 micron wavelength, or long-wave IR (LWIR), 8 to 12 micron wavelength, regions to observe the temperature of the environment surrounding an explosive particle. Thermal imaging sensors employing detection in the MWIR region benefit from superior resolution and contrast while those detecting in the LWIR region offer enhanced sensitivity to smaller temperature fluctuations and are less affected by atmospheric conditions (e.g., LWIR radiation can be transmitted through mist and smoke).

For trace explosive decomposition, the inherently small particle sizes complicate the detection process. For an explosive compound undergoing anaerobic thermal decomposition, the heat released is expected to be equivalent to about a 100° C. temperature rise in a 200° C. environment within a five to five hundred millisecond time frame, depending upon the type of explosive, its mass, the heating rate and the rate of heat loss. In some cases, the time frame is 5 to 30 milliseconds. If all of the exothermic energy produced by the decomposition of the explosive occupied one instantaneous field of view (IFOV) of the IR detection array, this would be easily detectable, since most MWIR/LWIR sensors have sensitivities near 0.05° C. However, trace amounts of explosive particles emitting this heat may weigh as little as a few nanograms and their emitted energy may only occupy a region 0.1 to 0.01 millimeters in diameter. Since the IFOV per pixel of a typical sensor lens is about two millimeters in diameter at close range (approximately one foot away from the source), the released energy from a trace explosive is undetectable across the IFOV area. In this case, the temperature rise has been diluted across the entire IFOV and appears as a temperature increase as small as 0.003° C. for a nanogram-size particle.

In one implementation, in order to detect localized heat signatures, an IR detection array is appropriately configured to record fast, microscopic reactions. Because of these constraints, the IR sensor 140 has a macro (close-up) lens capable of achieving an IFOV of less than between 50 and 150 microns in diameter per pixel. In addition, the resolution of the IR sensor 140 is sufficient to provide numerous individual pixels which act as their own individual heat detectors and serve to increase the sensitivity of the detection of energetic particles. For example, doubling the resolution of the IR sensor 140 leads to a four to eight time reduction of the lower detection limit. If the IR sensor 140 integration time between frames is long relative to the energy release, the energy is time averaged and may not be captured by the sensor. For example, for a five to ten millisecond reaction and using a 60 Hz (16 ms) imaging rate, the observed energy released from an energetic particle is reduced by less than a factor of 3.

In one implementation, the IR sensor 140 includes a long wave infrared detector (LWIR) that is sensitive in the 7.5 to 14 micron range. The detector is equipped with a focusing lens in order to resolve pixels down to about 50 microns. The refresh rate of the system is 60 Hz. The detector is a 320×240 array with 76,800 pixels. The sensitivity of each pixel is specified as 0.05° C., which facilitates sensitivity at the mid-picogram level. Since the particle mass is inversely proportional to the third power of the pixel size, the sensitivity can be enhanced by using a more powerful focusing lens.

The previous description provides an exemplary implementation of a decomposition system. Other implementations may include other or different features. For instance, the collection material 120 may be an individual sample which is clamped down for heating.

Figure 2:
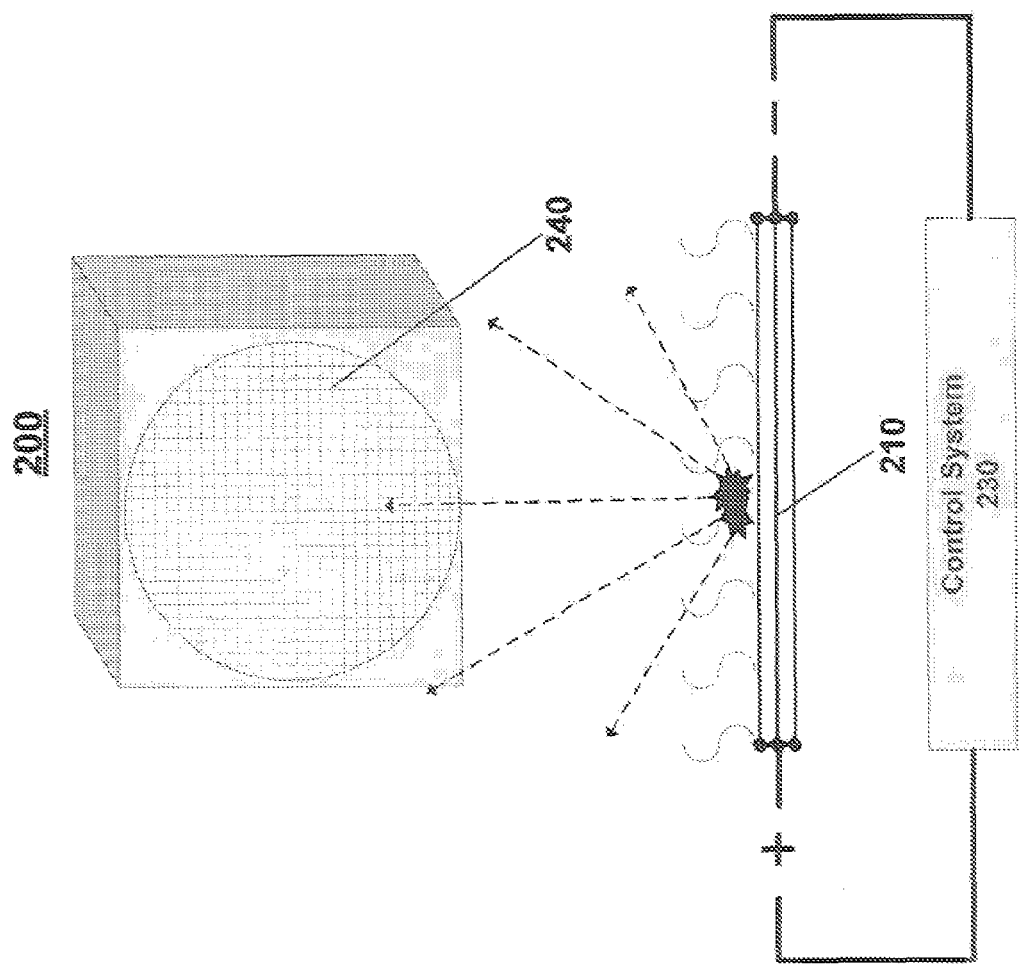
FIG. 2 illustrates a detection system employing resistive heating.

Referring to FIG. 2, a detection system 200 employing resistive heating includes a conductive collection material 210, a control system 230 and an IR sensor 240. In the system 200, an electrical current is run through the collection material 210, which heats due to inherent resistance and triggers energetic decomposition of the sample.

The control system 220 directs the flow and duration of current through the conductor 210. Depending on implementation, varying types of current signals may be produced by the control system 220. A step current may be used to quickly adjust the current to a desired level and is useful in triggering all explosive materials to decompose quickly with minimal oxidation in an atmosphere.

In other implementations, a ramp current that increases at a constant rate is used. Since thermal decomposition is triggered at differing energy levels for differing explosive materials, ramped current enables the system 200 to more precisely determine the nature of the explosive. Other currents shapes, such as, for example, plateaus, may be included to determine further characteristics of the sample.

A rapid heating rate facilitates near anaerobic heating conditions, as oxygen requires time to reach the reaction site. In particular, when heating a sample in an atmosphere with ambient oxygen (e.g., air), rapid heating (e.g., tens of milliseconds to a second), such as the heating produced by a step current, is desirable to avoid combustion or oxidation of non-explosive particles. When heated slowly enough to allow oxygen to reach the reaction site (e.g., a few seconds), contaminants, such as diesel fuel or sugar, may combust or oxidize (e.g., combust aerobically). Since explosive materials include the required oxygen for combustion within their chemical structure or mixture, thermal decomposition is generally triggered before any combustion with ambient air, during rapid heating.

In one particular implementation, the conductive collection material 210 is a 400 mesh, 316 grade stainless steel, which includes an opening that is 38 microns between wires. The mesh is heated electrically using a power supply operating at 4.5 volts and approximately 22 amps while an IR sensor is focused onto the mesh using a 0.5× macro germanium lens with a nominal resolution limit of 90 microns. The data is collected at 60 frames per second via a Firewire connection between the IR detector and the data collection electronics.

The previous description provides an exemplary implementation of a decomposition system employing resistive heating. Other implementations may include other or different features. For instance, the conductive collection material 210 may be replaced with a heat resistant collection material attached to a conductor. Also, heating sensing devices connected to the control system may detect the heat level. The detected heat level may be used to generate a feedback loop with the control system.

Figure 3:
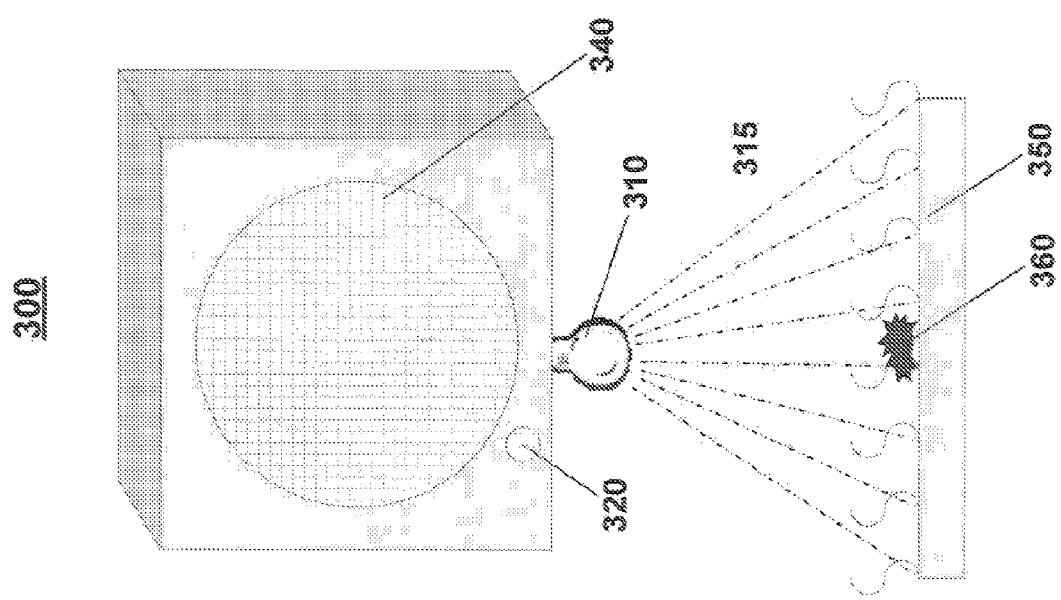
FIG. 3 illustrates a detection system employing radiative heating.

Referring to FIG. 3, a detection system 300 employing radiative heating includes a radiation device 310, a pyrometer 320, an IR sensor 340 and a sample medium 350 that carries a sample 360. In the system 300, radiation 315 is directed to the sample medium 350. Struck by the radiation, the sample medium 350 heats and thermal decomposition of sample 360 is triggered.

The intensity or duration of the emitted radiation 315 by the radiation device 310 may be based upon measurement of the pyrometer 320, which measures the rapid heating of the sample 360 in real-time. In one implementation, the radiation device 310 is a flash-lamp, which may rapidly release enough energy to trigger thermal decomposition. By varying the power level and material used, flash-lamp implementations may be used to flash objects at several meters. If an infrared laser, such as q-switched niobium YAG system, is used to heat the sample 360, the heating may be conducted over great distances (10-100s of meters).

The previous description provides an exemplary implementation of a decomposition system employing radiative hearting. Other implementations may include other or different features. For instance, the radiative system may be designed to release set amounts of energy without requiring a pyrometer for control.

Figure 4:
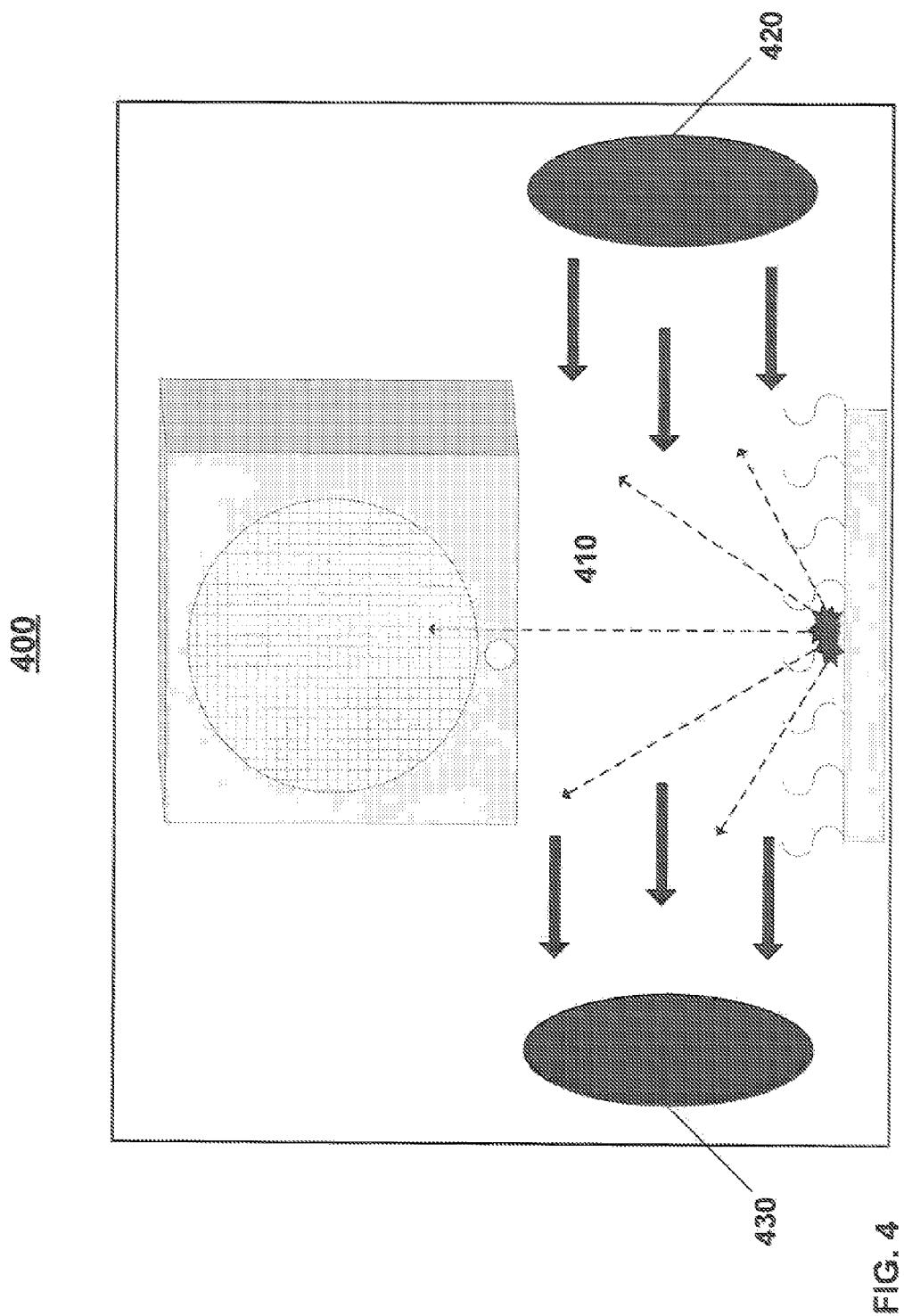
FIG. 4 illustrates a detection chamber employing atmospheric alteration.

Referring to FIG. 4, a detection chamber 400 employing atmospheric alteration, includes an input vent 420 and an output vent 430 to generate an altered atmosphere 410 in the chamber 400 by reducing air-pressure, introducing non-reactive gases, or both. The altered atmospheric 410 features less ambient oxygen available for combustion or oxidation with contaminants.

The input vent 420 is optional, and introduces non-reactive gases, such as, for example, nitrogen or neon, into the atmosphere. The non-reactive gases decrease the availability of gaseous oxygen for combustion or oxidation. The output vent 430 removes gas to lower pressure, and, consequently, lower the amount of gaseous oxygen in the chamber 400. By employing the input and output vents 420 and 430, the chances of contamination are lowered, and heating to trigger thermal decomposition may be slowed to levels that would create combustion in air. The chamber 400 may be particularly useful in implementations employing a slow ramp or plateau style of heating.

The previous description provides an exemplary implementation of a decomposition chamber employing atmospheric alteration. Other implementations may include other or different features. For instance, the chamber may be designed to simply remove the atmosphere without requiring an input vent.

Figure 5:
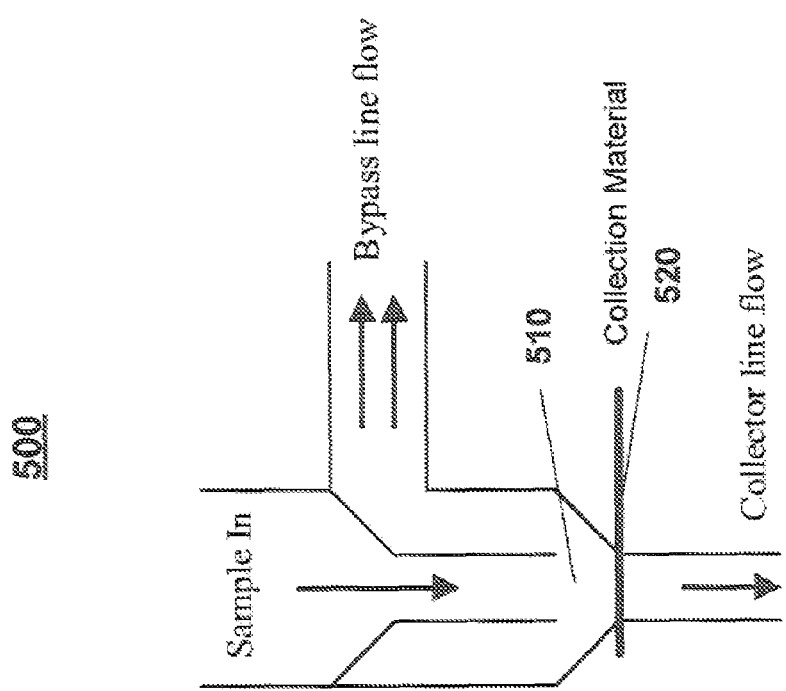
FIG. 5 illustrates an impact collector.

Referring to FIG. 5, an impact collector 500 may be used to deposit one or more air streams of vacuumed samples including explosive particles onto a collection material 520 which may be analyzed as described in the decomposition system 100 with respect to FIG. 1. The air streams may be generated by vacuuming an object, such as clothing, luggage, or an individual's skin, that is to be tested. In the impact collector 500, there is a critical flow to avoid particles falling out of the airflow and onto the tubing walls. One implication of particles falling out of the sample stream is a loss of sample that leads to a false negative. Another implication is one of carry over. Specifically, if a particle falls out of the sample stream, the particle has the potential of showing up in later samples leading to a false positive. Because of such implications, after every positive sampling, there may be a clearing purge cycle, where the system is run without additional sample material.

In the impact collector 500, the air and explosive vapors divide according to the ratio of the bypass flow to the collector flow. Typical collector flows are between 0 and 10 percent of the total flow. Particles, however, are not able to make the 180° turn 510 and thus impact upon the collection material 520. In order to keep the piping of the turnstile clean, valves may be placed downstream of the collection system and kept closed except during the sampling time.

In one particular implementation, the internal inner-diameter of the impact collector 500 is about 1.5 cm. The outer ring is about 3 cm in diameter. If the collection material 520 rotates, the impact collector 500 itself needs to clear the collection material 520. The impact collector 500 may need to seal against the portion of the collection material 520 at the outer ring with the inner tube being from about 0.2-2.0 cm away from the collection material 520. An O-ring may be included on the outer tube to form a seal. In come cases, slight leakage may be acceptable. Depending on implementation, either the impact collector 500 is lowered to form the seal, or the collection material 520 itself is raised to form the seal.

Once the deposition has occurred, the collection material 520 or a portion of the collection material 520 may be heated to trigger decomposition.

Figure 6B:
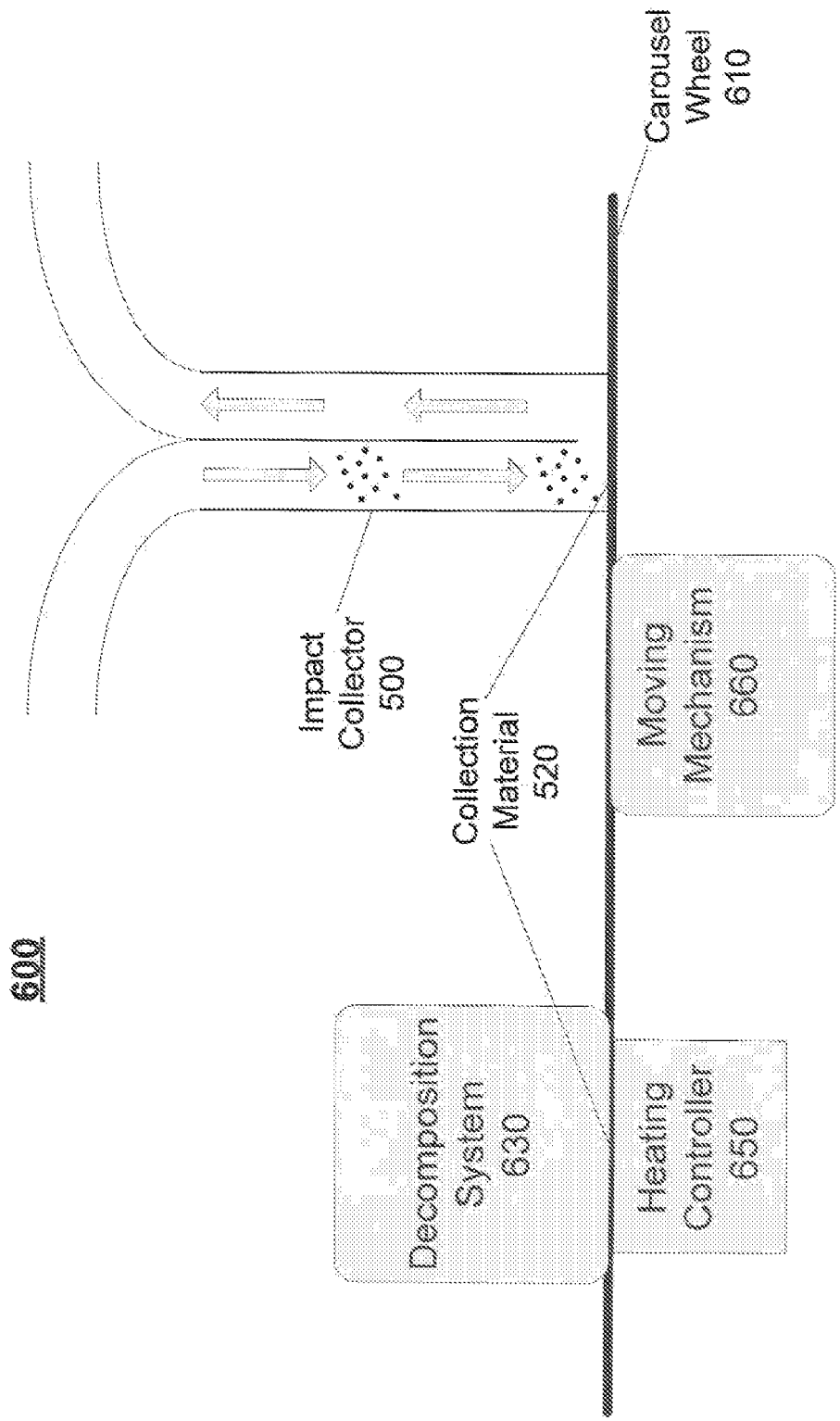

Referring to FIG. 6A, a top view of a collection and detection system 600 includes the impact collector 500 and collection material 520 of FIG. 5, and a decomposition system 630. The decomposition system 630 may be any of the systems 100-400 of FIGS. 1-4. In the collection and detection system 600, the impact collector 500 is used to deposit the sample onto the collection material 520. A media moving mechanism 660 (FIG. 6B) moves the collection material 520, which is mounted on a carousel wheel 610, such that the collection material 520, including the sample, moves from a region adjacent to the impact collector to a region within the decomposition system 630. The deposited material is than analyzed for traces of a specific material.

Referring to FIG. 6B, a side view of a collection and detection system 600 includes a heating controller 650 and the media moving mechanism 660. The discussion below refers to two specific implementations directed to resistive and radiative heating exothermic decomposition, but other methods of initiating thermal decomposition may also be used. In particular, elevating the temperature of a particle by using electromagnetic radiation, lasers, the convection of heat via warm air to the particle, or the conduction of heat to the particle would be sufficient for causing thermal decomposition.

The particular collection and detection system 600 to be used may be based on factors such as a desired period between maintenance sessions, ease of maintenance, or cost. FIGS. 6A-6B illustrate an implementation involving a carousel wheel 610 with a reusable discreet collection material 520. Other implementations, such as a "reel-to-reel" system with a one time or reusable collection material 520, also may be used. Such a reel-to-reel mechanism may be more costly to build and more difficult to maintain (e.g., by replacing the worn collection material 520) than the carousel wheel 610. Because the reel-to-reel mechanism could hold more collection material, the time between replacements may be greater than for the carousel implementation.

In the illustrated implementation including a carousel wheel 610, the collection material 520 is within the carousel wheel 610 and includes either a series of discreet collecting areas or a continuous collecting area. In a series of steps, the collection and detection system 600 gathers collected material onto an area of the collection material 520 and then rotates to the decomposition system 630 to enable the deposited material to be analyzed to detect the presence of particles of materials.

According to various implementations employing the carousel wheel, a first station is the impact collector 500, which may seal to the carousel wheel 610. The term "station" refers to specific locations or degrees of rotation of the carousel wheel 610. The position of stations may be determined by the position of holes along the circumference at angular positions of the carousel wheel 610. After particles are deposited with the impact collector 500 to an area of the collection material 520, the carousel wheel 610 rotates to the second station, which is the decomposition system 630. Characteristics of the decomposition system 630 depend on the detection unit employed.

A media moving mechanism 660 is employed to rotate the collection material 520, and in the implementation discussed above, the carousel wheel 610. For a high degree of positional accuracy, a stepper motor may be employed. As a stepper motor is expensive and requires specialized electronics to control, a simpler alternative that may be used is a unidirectional or bidirectional DC motor. An LED optical sensor may be used to determine and control the position of the media moving mechanism 660. Maintenance of the carousel wheel 610 may be conducted through an automatic disc loading and unloading station to extend the time between routine replacement of the collection material 520 to, for example, one month.

In one implementation that includes resistive heating, the collection material 520 area is three $cm^2$ and includes two contacts which are placed at opposite ends of the collection material 520. The contacts may be shaped in various ways, such as, for example, raised metallic bumps (e.g., like a contact for a battery), rods, or plates. A spring loaded contact may be used to complete the connection. The carousel wheel 610 may be designed with upper and lower halves. In one assembly method, the two halves are separated, the collection material 520 is installed on the bottom half, and the top half is attached on top of the collection material 520 forming a sandwich. In one implementation, for each portion of the collection material 520, one of the contacts is in the form of an electrode which is tied to a single common connection point (not shown), and the other contact 660 is a unique connection. In such an implementation, the common connection point is constantly connected to the power supply, and only one unique connection is connected at a time to enable only one portion to be resistively heated. The collection material 520 may include holes for the optical sensors (or LED sensor as discussed above with respect to the carousel wheel 610 implementation).

Residual material, such as oils, may contaminate or mask later measurements, or may shorten the life of a reusable collection material 520. By heating the collection material 520 to a higher temperature than that required to trigger decomposition of energetic material, such residual material may be burned off. Optionally, a high temperature bake out at temperatures in excess of 300° C. may be conducted in order to thermally decompose remaining particles.

A pyrometer may be included in the decomposition system 630 or the heating controller 650. During heating, there is slight expansion of the collection material 520. In order to prevent distortion, the design is such that there is a slight tension on the collection material 520.

Figure 6C:
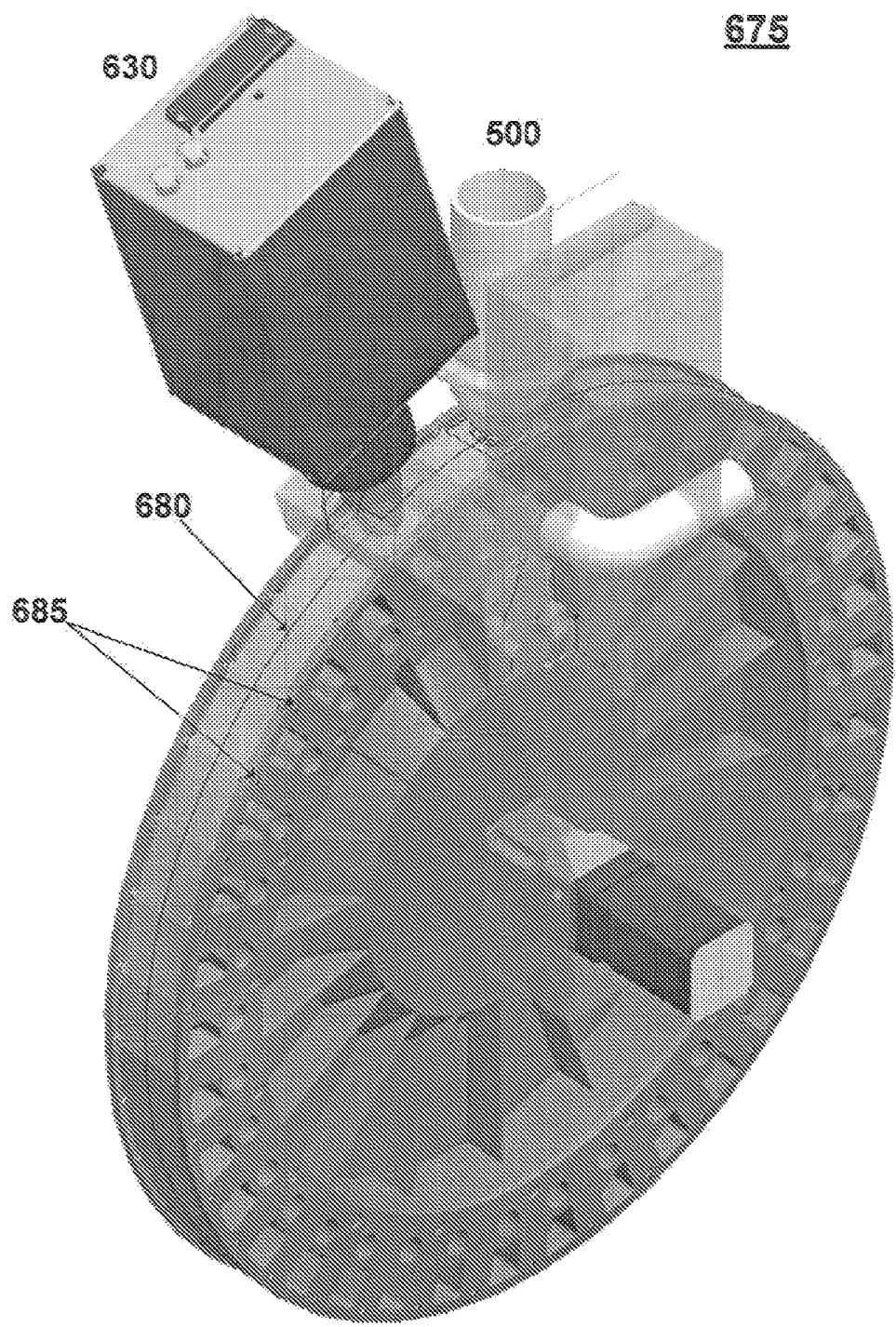
FIG. 6C illustrates a collection and detection system with a continuous collection material.

Referring to FIG. 6C, a continuous collection material system 675 includes a continuous conductive collection material 680, and discrete contact points 685. In the system 675, the continuous material 680 is wrapped around the width of a wheel. A portion of the continuous material 680 is within the impact collector 500 where particles may be deposited. As the wheel rotates, the portion moves within the decomposition system 630.

The continuous system 675 includes numerous discrete contact points 685 where an electrical connection is established. When the decomposition system 630 is activated, discrete contact points 685 are used to generate a current through the continuous material 680, resistively heating the particles. In order to prevent an electrical path through the full circumference of the continuous material 680, a portion of the continuous material 680 may be left black or otherwise severed.

The previous description provides exemplary implementations of a collection and detection system 600. Other implementations may include different features, such as a checking solution injected onto the collection material 520 on an infrequent but scheduled basis to test the ability of the system to successfully detect particles of a material. This mechanism may include a reservoir that needs to be replaced periodically and may include, for example, a LEE miniature variable volume pump model LPVX0502600B, (see www.theleeco.com) or a small KNF model UNMP830 (see www.knf.com) or similar pump and a LEE solenoid valve similar to LEE model number INKX051440AA.

Figure 7A:
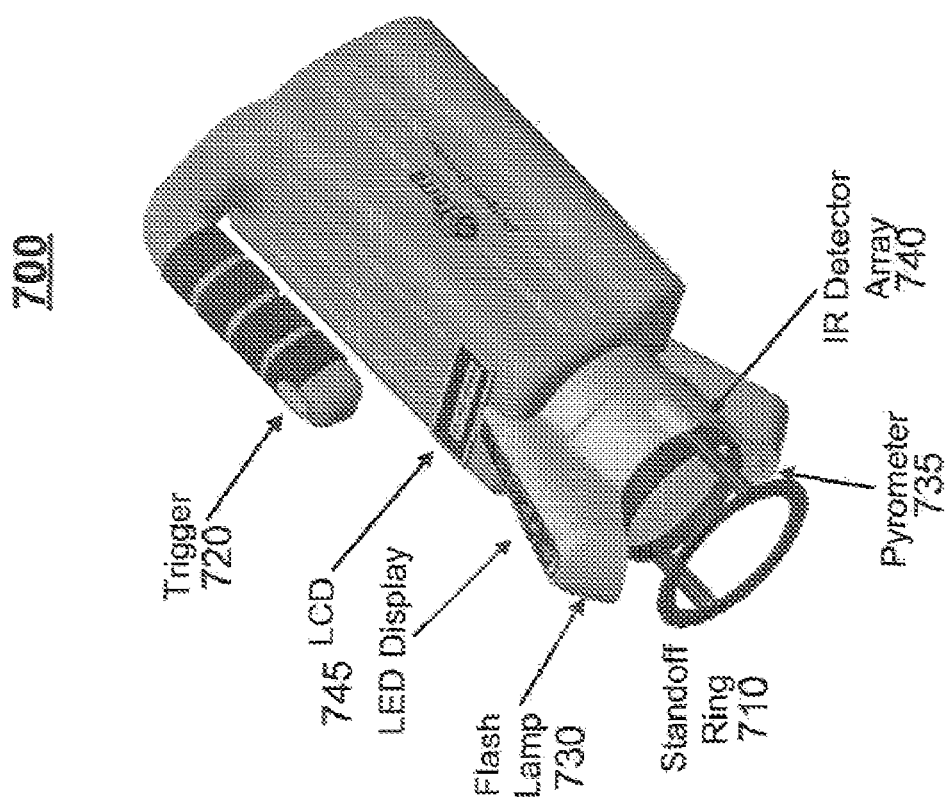
FIG. 7A illustrates a hand-held detection system.

Referring to FIG. 7A, a hand-held detection device 700 includes a standoff ring 710, a trigger 720, a flash-lamp 730, a pyrometer 735, an IR-detector array 740, and output displays 745. The device 700 may be brought to the sample in order to detect explosive particles.

In order to operate the device 700, the user first places the standoff ring 710 on the area to be scanned for explosive particles. The standoff ring 710 provides an appropriate distance between the sample and the IR detector array 740. Next, the user operates a trigger 720 to activate the flash-lamp 730 and cause heating. The flash-lamp 730 is aimed at the standoff ring 710 and heats the sample to trigger thermal decomposition. The real-time temperature of the sample is measured through the pyrometer 735, and such measurement is a part of a feedback loop to enable the temperature to be actively controlled by the flash-lamp 730. The IR-detector array 740 detects decomposition by explosive materials. The detected results are indicated by the output displays 745.

Figure 7B:
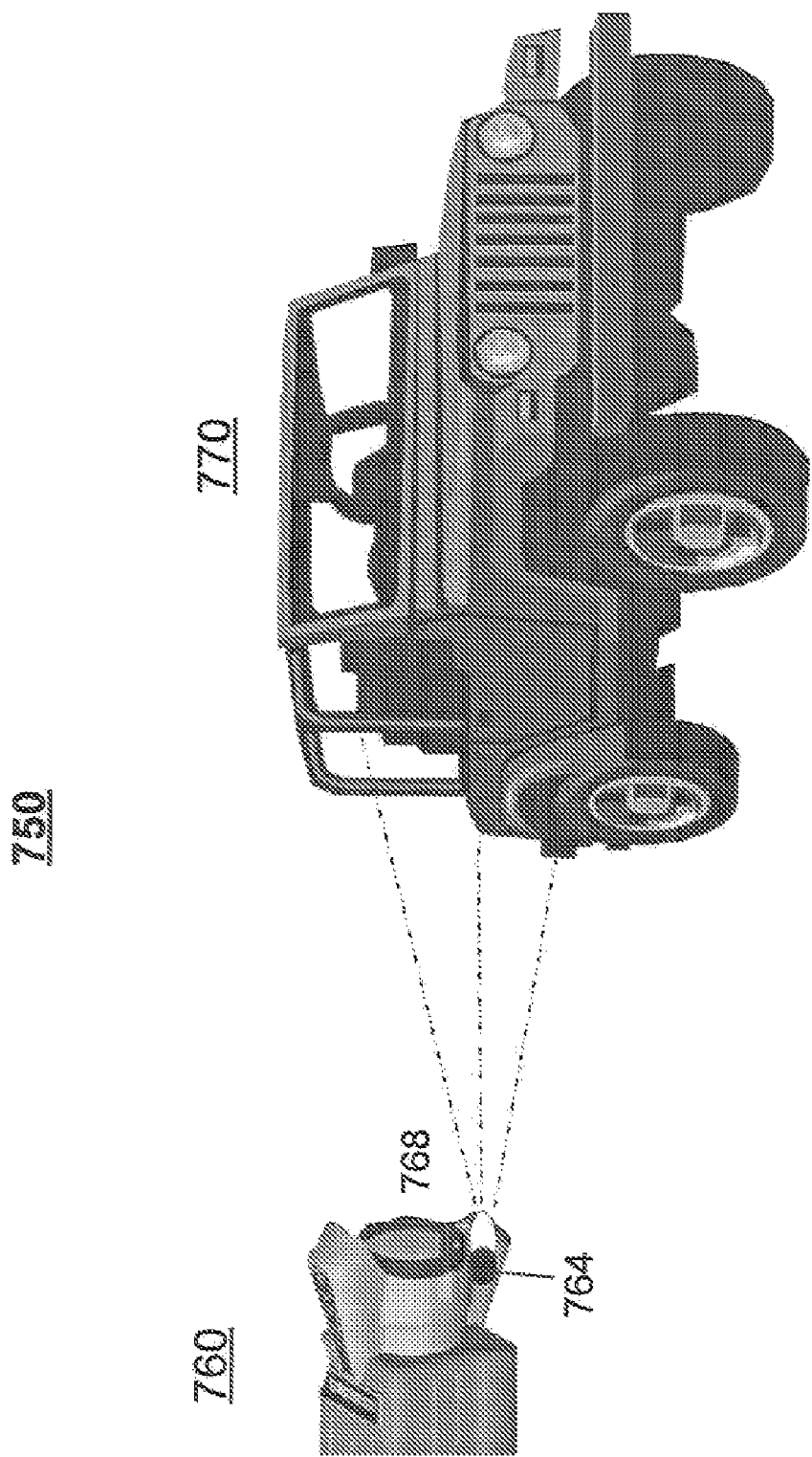
FIG. 7B illustrates a ranged detection system.

Referring to FIG. 7B, a long-range detection system 750 includes a detection device 760 that operates as described above and may be aimed at an object 770 at a distance. In the system 750, the detection device 760 emits radiation in the direction of the object 770. After striking the object 770, the radiation causes localized heating that triggers thermal decomposition of trace explosive particles. IR radiation released from the decomposition is detected by the detection device 760.

In particular, the detection device 760 includes a flash-lamp 764 and a distance focused IR detector array 768. The flash-lamp 764 emits a pulse of high-energy radiation sufficient to cause thermal decomposition at the object 770. Emitted IR radiation strikes the IR detector 768 which enables a positive identification of trace explosives.

The detection device 760 may be enabled to operate at a distance of tens to hundreds of meters from the object 770. Laser heating may be used as an alternative to flash-lamp heating. Laser hardware may be considerably more complex, power consuming, and expensive than hardware required for resistive or flash-lamp heating. As such, the use of a laser may be practical mainly in implementations where the object 770 is at a considerable distance beyond the immediate vicinity of the detection device 760. Also, a telephoto lens may be included that focuses the IR detector array 768 on an appropriately small area. In one implementation, the telephoto lens focuses the IR detector array 768 such that the array views the object 770 at a resolution that is similar to the resolution of FIG. 1.

In one implementation, a checkpoint for explosives equips a detection device 760 to detect vehicles for explosives. The detection includes operation of the flash-lamp across the sides of vehicles to detect explosives along various areas of the object 770 being scanned.

The previous descriptions provide exemplary implementations of handheld and range detection devices. Other implementations may include other, or different features. For example, various implementation, the detection device may be mounted in a variety of vehicles, such as, for example, an armored personal carrier, a tank, an aircraft, or a seacraft.

Figure 8B:
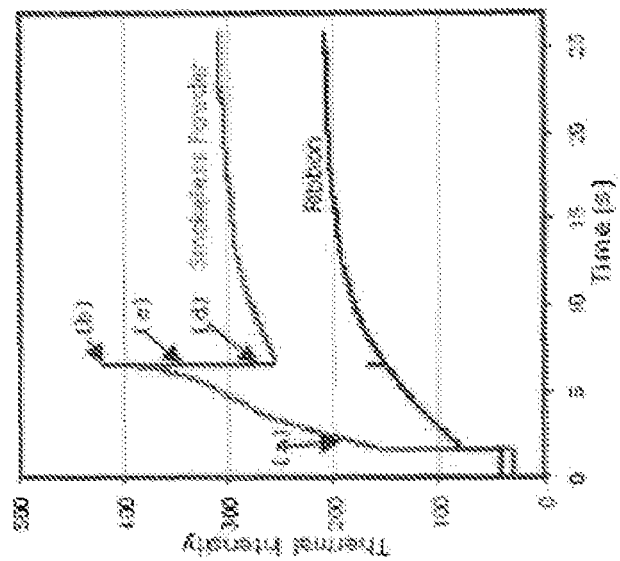
FIGS. 8A and 8B illustrate particle detection data.
Figure 8A:
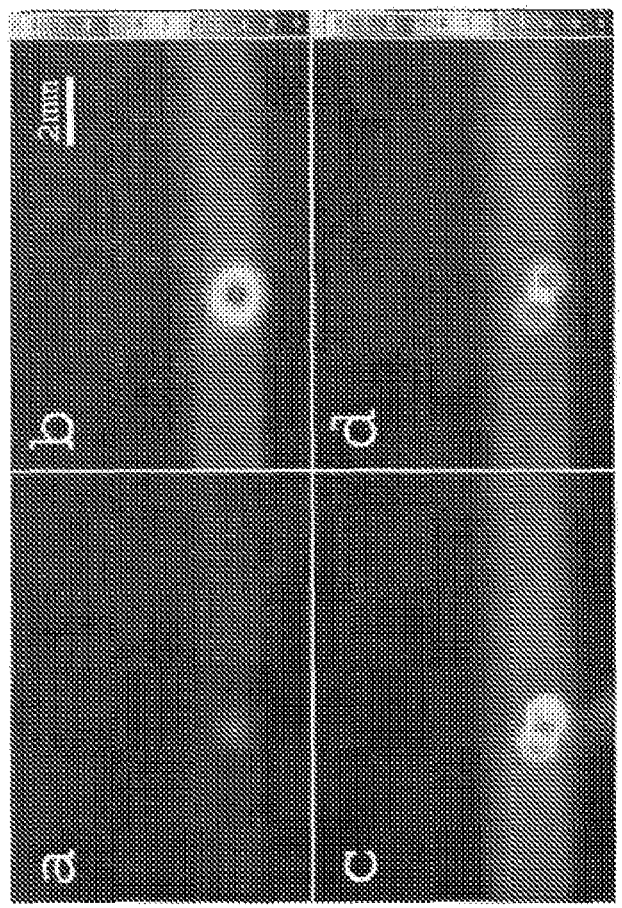

FIG. 8A shows data 800 of an exothermic decomposition detection. In particular, a picture is shown of a sample media with a decomposing material at four different instances of time. Specifically, data 800 for the energetic detection of a particle of smokeless powder using a 60 Hz frame rate are shown. Element (a) shows an initial IR image with a relatively cool particle and filament. Next, element (b) shows an IR image showing elevated temperatures around the particle just prior to explosion. Next, element (c) shows an IR image showing the particle explosion. Finally, element (d) shows an IR image showing elevated gas temperatures resulting from the particle explosion.

Referring to FIG. 8B, data 850 for the same decomposition are shown from the perspective of a pixel viewing the smokeless powder and a pixel viewing the sample media across time. In the data 850, the four instances of time from the data 800 of FIG. 8A are marked. Specifically, two-dimensional plots of the thermal signatures of one pixel viewing the smokeless powder and one pixel viewing the sample media are shown.

Analytical interpretation of the results is possible by examining the temperature of individual pixels or the average of several pixels as a function of time. Results may demonstrate that a particle's rapid increase in temperature exceeds that of the collection material. This feature can be used in algorithms to automatically detect the presence of explosives. In particular, each energetic compound has a quantifiable and positive heat of decomposition (H) and a quantifiable activation energy (E). H impacts the total heat that is released and E the rate of heat release. These two properties interact in such a way that a detector may distinguish classes of explosives and/or the chemical composition.

Automatic algorithm based target recognition is used to track multiple pixels simultaneously and to automatically recognize the unique characteristics of explosives. Simple enhancements include subtraction of the varying background temperature, and displaying the differential so as to better visualize the peak maximum. Local maxima and/or minima in a temperature versus time plot are indicative of the presence of explosives and are mathematically defined as points at which the time rate of change of the temperature equals zero (i.e., $dT/dt=0$). However, local maxima due to the fluctuating temperature of the collection material may also be present. To correct for these artifacts, the collection material temperature may be subtracted from the temperature recorded at various points.

Figures 9A, 9B:
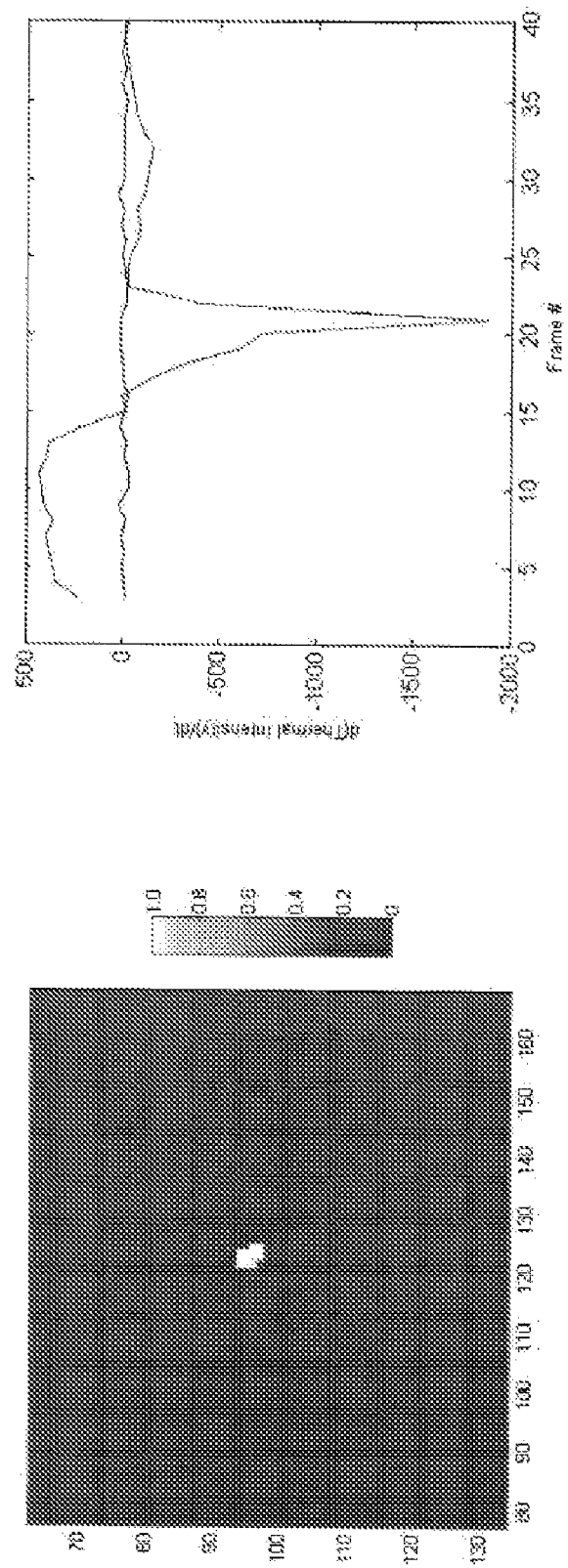
FIGS. 9A and 9B illustrate processed particle detection data.

FIG. 9A shows processed data results 900 of a detected exothermic decomposition. To determine the results 900, an algorithm is used to analyze the time derivative of the raw data for a threshold level that is characteristic of an explosive. The raw data was obtained by heating 100 nanograms of triacetone triperoxide (TATP) to trigger exothermic decomposition. As seen from the image, approximately 12 pixels exceeded a threshold analytically determined by the algorithm. This level of response for TATP correlates to a detection limit of 8 nanograms/pixel.

Referring to FIG. 9B, the plot 950 shows a pixel at (95, 123) with a background pixel at (110, 140), from the processed data results 900 of FIG. 9A. Detection of RDX, TNT, TATP and ANFO have all been verified at the 100, 25 and even sub 10 ng level on dirty substrates under conditions typical of use. Detection has also been demonstrated for explosive materials such as PETN, Benzoyl Peroxide, ammonium perchlorate and smokeless powder.

Testing was also performed for potential interference materials such as sugar, diesel fuel, gasoline, numerous hand creams and lotions, perfumes, dandruff, human skin oils, wipings of sweat from the back of the neck, and fingerprints from touching salami, bacon and other preserved meat and fish products, all of which gave a clear "no-alarm" signal.

Figure 10:
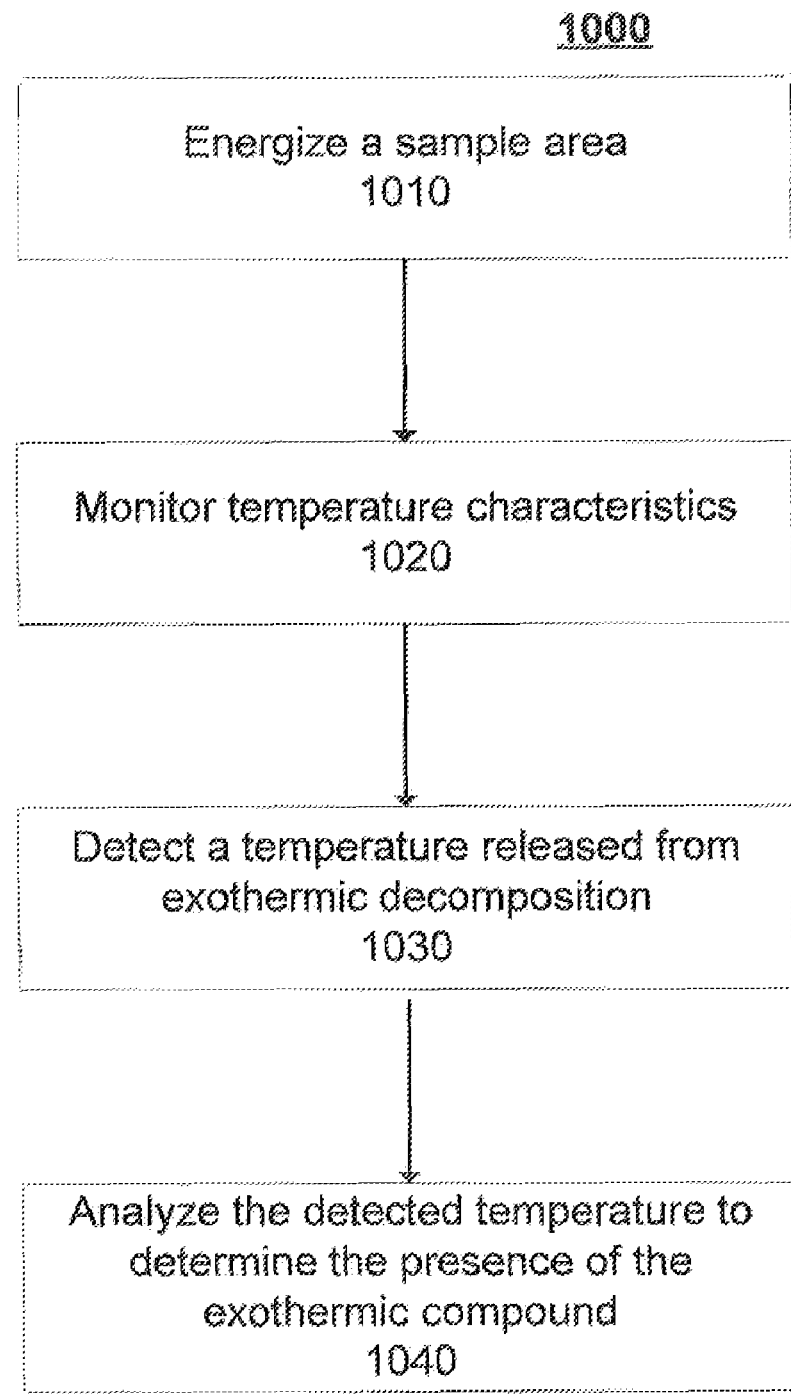
FIG. 10 is a flow chart of a method of detecting energetic materials.

Referring to FIG. 10, detecting energetic materials, such as explosives, includes energizing a sample area, monitoring temperature characteristics, detecting a temperature released from exothermic decomposition, and analyzing the detected temperature to determine the presence of the exothermic compound.

A sample area is energized (step 1010). As shown with respect to FIGS. 2 and 3, energizing the sample area may include resistive or radiative heating. When the sample area is at a large distance from the energizing mechanism, other methods, such as lasers may be used.

Temperature characteristics of the sample area are monitored (step 1020). Energy corresponding to the sample area's temperature may be detected by using a sensor focused on the sample area. An infrared sensor may be used to sense infrared emissions from the sample area as well as a surrounding material or collection area.

A temperature released from exothermic decomposition is detected (step 1030). Specifically, as an exothermic compound in the sample area heats, the exothermic compound may undergo thermal decomposition. Energy released from the thermal decomposition may be detected by the sensors monitoring the temperature characteristics.

The detected temperature is analyzed to determine the presence of the exothermic compound (step 1040). The analysis may include determining a temperature difference between an area and its surroundings, or a time rate of change of temperature. The analysis also may include determining a heat of decomposition or an activation energy of the thermal decomposition. Determined information may be used to determine a specific type or category of explosive that underwent exothermic decomposition.

Various implementations employ several other benefits. For example, the performance of the detector may not be adversely affected by the presence of a massive overload of background materials. In particular, there may not be degradation in performance when the sample is coated in oily substances and even when smoke is clearly visible. With the detector, there may be immediate recovery from massive overloads as big as 2,000 ng of material. Further, the detector may detect chemicals that conventional detectors may miss, such as, ammonium nitrate, nitro cellulose, TATP, benzoyl peroxide, ammonium perchlorate, other explosive chemicals, or mixtures of unknown chemistry. In general, if a material can explode, the material's presence may be detected through thermal decomposition.

Other implementations are within the scope of the following claims.

What is claimed is:

1. A method of detecting explosive materials, the method comprising:
   providing energy to a sample area such that the rate with which energy is provided triggers anaerobic exothermic decomposition of particles of explosive materials of the sample area before other particles of the sample area are aerobically combusted with ambient oxygen;
   detecting energy released from decomposition of particles of the sample area which analyzing the detected energy for one or more characteristics indicative of anaerobic exothermic decomposition; and
   determining whether the particles of explosive materials are present on the sample area based on the analysis of the detected energy for characteristics indicative of anaerobic exothermic decomposition.

2. The method of claim 1 wherein providing energy to the sample area includes resistively heating the sample area.

3. The method of claim 2 wherein resistively heating the sample area includes generating a current through a conductive collection material.

4. The method of claim 3 wherein the conductive collection material is a metal mesh, wherein:
   generating the current through the conductive collection material includes generating the current through the metal mesh.

5. The method of claim 3 wherein generating the current through the conductive collection material includes generating a step current.

6. The method of claim 1 wherein providing energy to the sample area includes radiatively heating the sample area.

7. The method of claim 6 wherein radiatively heating the sample area includes flashing the sample area with a flashlamp.

8. The method of claim 6 wherein radiatively heating the sample area includes using a laser.

9. The method of claim 6 wherein radiatively heating the sample area includes radiatively heating the sample area from a distance beyond the adjacent vicinity of the device used to radiatively heat the sample area.

10. The method of claim 1 wherein detecting the energy released from decomposition of the particles of the sample includes monitoring infrared radiation released from the decomposition of the particles of the sample area.

11. The method of claim 1 wherein detecting energy released from decomposition of the particles includes detecting energy released from exothermic decomposition of triacetone triperoxide.

12. The method of claim 1 wherein analyzing the detected energy includes analyzing energy data for the difference between an energy level of a first pixel and a background pixel.

13. The method of claim 1 wherein analyzing the detected energy includes analyzing the change with respect to time of energy data.

14. The method of claim 1 wherein analyzing the detected energy for one or more characteristics indicative of anaerobic exothermic decomposition includes analyzing energy data to determine a heat of decomposition of the particles of explosive material that underwent anaerobic exothermic decomposition.

15. The method of claim 1 wherein analyzing the detected energy includes analyzing energy data to determine an activation energy of the particles of explosive material that underwent anaerobic exothermic decomposition.

16. The method of claim 1 further comprising using a determined heat of decomposition or activation energy to determine a specific type or category of material that underwent anaerobic exothermic decomposition.

17. The method of claim 1 further comprising lowering atmospheric oxygen available for combustion.

18. The method of claim 17 wherein lowering the atmospheric oxygen includes reducing air-pressure.

19. The method of claim 17 wherein lowering the atmospheric oxygen includes introducing non-reactive gases.

20. The method of claim 1 wherein providing energy to the sample area such that the rate with which energy is provided triggers anaerobic exothermic decomposition of particles of explosive materials before other particles are aerobically combusted with ambient oxygen includes providing energy to a sample area without altering the atmosphere to which the sample area is exposed.

21. A system for detecting explosive materials, the system comprising:
   a sample energizer configured to provide energy to a sample area such that the rate with which energy is provided triggers anaerobic exothermic decomposition of particles of explosive materials of the sample area before other particles of the sample area are aerobically combusted with ambient oxygen;

a sensor configured to detect energy released from decomposition of particles of the sample area; and an analyzing device configured to analyze the detected energy for one or more characteristics indicative of anaerobic exothermic decomposition and to determine the presence of the particles of explosive materials based on the analysis of the detected energy.

22. The system of claim 21 wherein the sample energizer is configured to resistively heat the sample area.

23. The system of claim 22 wherein the sample energizer is configured to generate a current through a conductive collection material.

24. The system of claim 23 wherein the conductive collection material is a metal mesh, wherein:

the sample energizer is configured to generate the current through the metal mesh.

25. The system of claim 23 wherein the sample energizer is configured to generate a step current through the conductive collection material.

26. The system of claim 21 wherein the sample energizer is configured to radiatively heat the sample area.

27. The system of claim 26 wherein the sample energizer is configured to flash the sample area with a flash-lamp.

28. The system of claim 26 wherein the sample energizer is configured to use a laser.

29. The system of claim 26 wherein the sample energizer is configured to radiatively heat the sample area from a distance beyond the adjacent vicinity of the device used to radiatively heat the sample area.

30. The system of claim 21 wherein the sensor is configured to monitor infrared radiation released from decomposition of the particles of the sample area.

31. The system of claim 21 wherein the sensor is configured to detect energy released from exothermic decomposition of triacetone triperoxide.

32. The system of claim 21 wherein the analyzing device is configured to analyze energy data for the difference between an energy level of a first pixel and a background pixel.

33. The system of claim 21 wherein the analyzing device is configured to analyze the change with respect to time of energy data.

34. The system of claim 21 wherein the analyzing device is configured to analyze energy data to determine a heat of decomposition of a material that underwent anaerobic exothermic decomposition.

35. The system of claim 21 wherein the analyzing device is configured to analyze energy data to determine an activation energy of a material that underwent anaerobic exothermic decomposition.

36. The system of claim 21 wherein the analyzing device is configured to analyze a determined heat of decomposition or activation energy to determine a specific type or category of material that underwent anaerobic exothermic decomposition.

37. The system of claim 21 further comprising an air-chamber configured to lower atmospheric oxygen available for combustion.

38. The system of claim 37 wherein the air-chamber is configured to reduce air-pressure.

39. The system of claim 37 wherein the air-chamber is configured to introduce non-reactive gases.

40. A system for detecting energetic materials, the system comprising:

energizing means for providing energy to a sample area such that the rate with which energy is provided triggers anaerobic exothermic decomposition of particles of explosive materials of the sample area before other particles of the sample area are aerobically combusted with ambient oxygen;

sensing means for detecting energy released from decomposition of particles of the sample area; and an analyzing device configured to analyze the detected energy for one or more characteristics indicative of anaerobic exothermic decomposition and to determine the presence of the particles of explosive materials based on the analysis of the detected energy.

41. The system of claim 21 wherein the sample energizer is configured to provide energy to a sample area without altering the atmosphere to which the sample area is exposed.

* * * * *

UNITED STATES PATENT AND TRADEMARK OFFICE
CERTIFICATE OF CORRECTION

| | | |
|---|---|---|
| PATENT NO. | : 7,645,069 B1 | |
| APPLICATION NO. | : 11/460586 | |
| DATED | : January 12, 2010 | |
| INVENTOR(S) | : David H. Fine et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 462 days.

Claim 1, line 56, delete the word "which" and insert a -- ; --.

Signed and Sealed this

Twenty-first Day of September, 2010

David J. Kappos
*Director of the United States Patent and Trademark Office*